United States Patent
Benje

(10) Patent No.: US 6,841,708 B1
(45) Date of Patent: Jan. 11, 2005

(54) METHOD OF PRODUCING ETHYLENE (DI) CHLORIDE (EDC)

(75) Inventor: Michael Benje, Darmstadt (DE)

(73) Assignees: Vinnolit Technologie GmbH & Co., Burgkirchen (DE); part interest; Uhde GmbH, Dortmund (DE); part interest (*) Notice: Subject to any disclaimer, the term of this patent is extended or adjusted under 35 U.S.C. 154(b) by 0 days.

(21) Appl. No.: 09/936,335

(22) PCT Filed: Oct. 12, 1999

(86) PCT No.: PCT/EP99/07649

§ 371 (c)(1),
(2), (4) Date: Sep. 12, 2001

(87) PCT Pub. No.: WO00/55107

PCT Pub. Date: Sep. 21, 2000

(30) Foreign Application Priority Data

Mar. 12, 1999 (DE) .......................... 199 10 964

(51) Int. Cl.$^7$ .............................. C07C 17/02
(52) U.S. Cl. ................ 570/247; 570/246; 570/252; 570/253; 570/254
(58) Field of Search .............. 570/246, 247, 570/252, 253, 254

(56) References Cited

U.S. PATENT DOCUMENTS 3,941,568 A 3/1976 Kurtz et al.
4,554,392 A 11/1985 Leuck et al.

FOREIGN PATENT DOCUMENTS

| DE | 1 905 517 | 8/1970 |
| DE | 24 27 045 | 1/1975 |
| DE | 25 40 257 | 4/1977 |
| DE | 40 39 960 | 9/1991 |
| EP | 0 026 349 | 4/1981 |
| EP | 471987 | * 2/1992 |
| EP | 0 471 987 | 2/1992 |
| JP | 06 157365 | 6/1994 |
| JP | 07 330639 | 12/1995 |

* cited by examiner

Primary Examiner—Johann Richter
Assistant Examiner—Elvis O. Price
(74) Attorney, Agent, or Firm—Collard & Roe, P.C.

(57) ABSTRACT

With a method or a device for producing 1,2-dichloroethane or ethylene (di)chloride (EDC) with the use of a circulating reaction medium and a catalyst, whereby ethylene and chlorine are supplied to the reaction medium, the goal is to permit the catalytic chlorination of ethylene in a manner that is particularly gentle to the product.

This is achieved in terms of the method and by other means in that the ethylene or chlorine gas are introduced into the reaction medium by means of microporous gas diffuser elements for producing gas bubbles with a diameter of 0.3 to 3 mm.

6 Claims, 3 Drawing Sheets

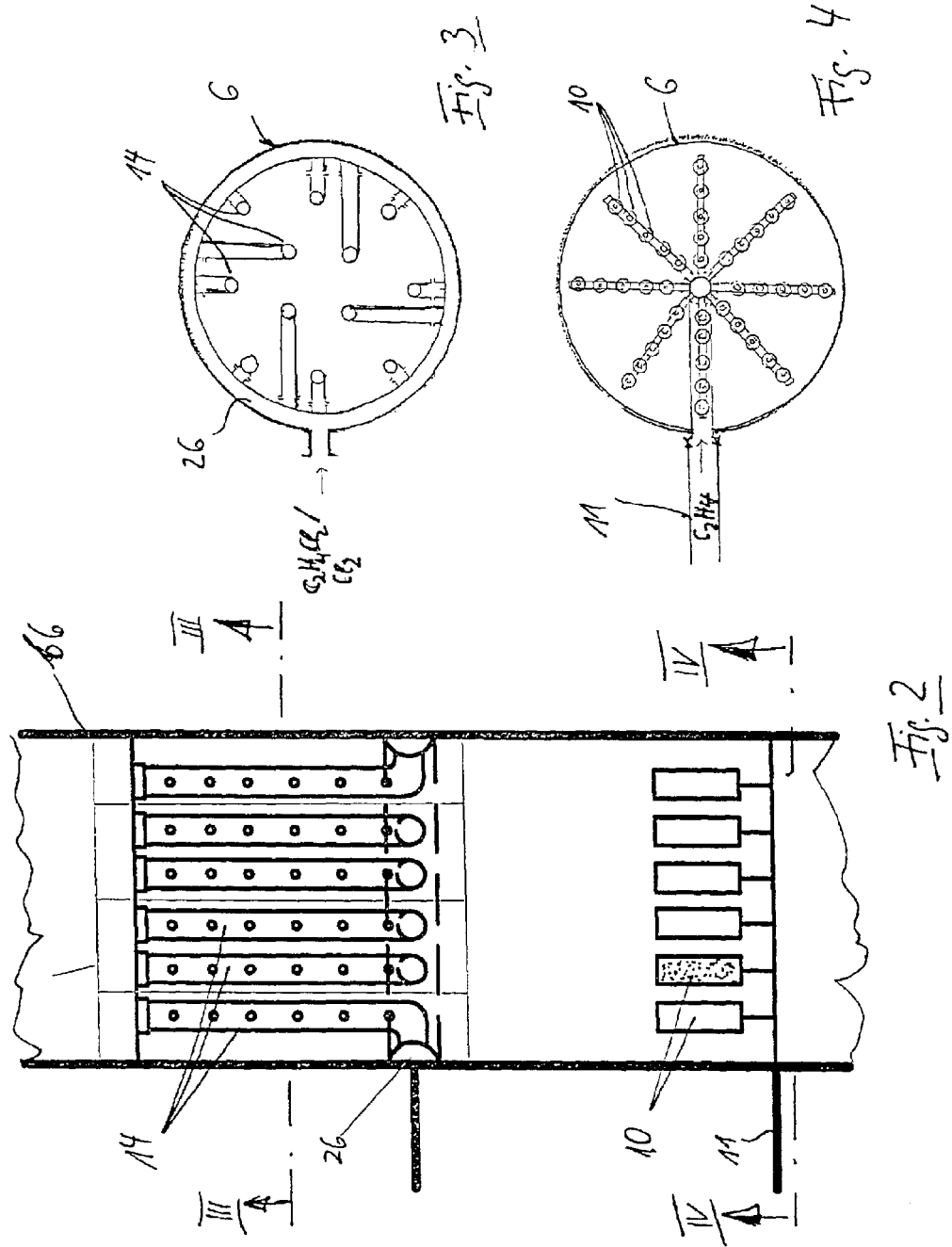

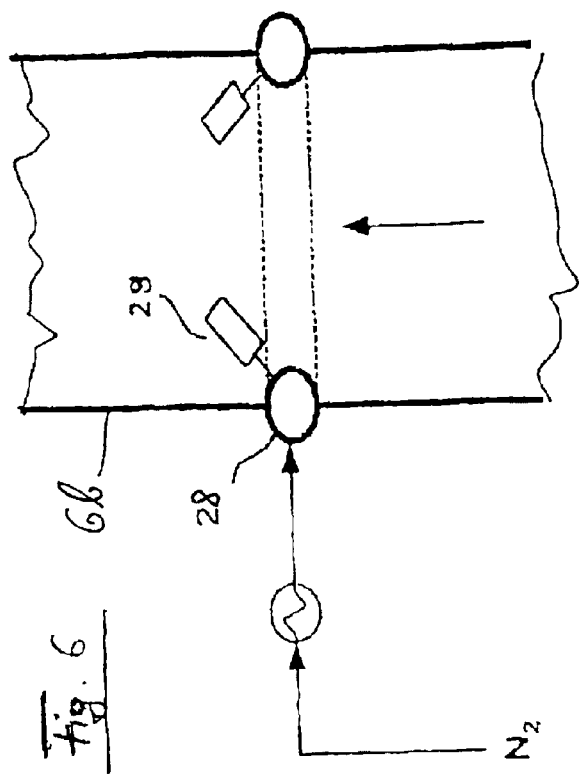
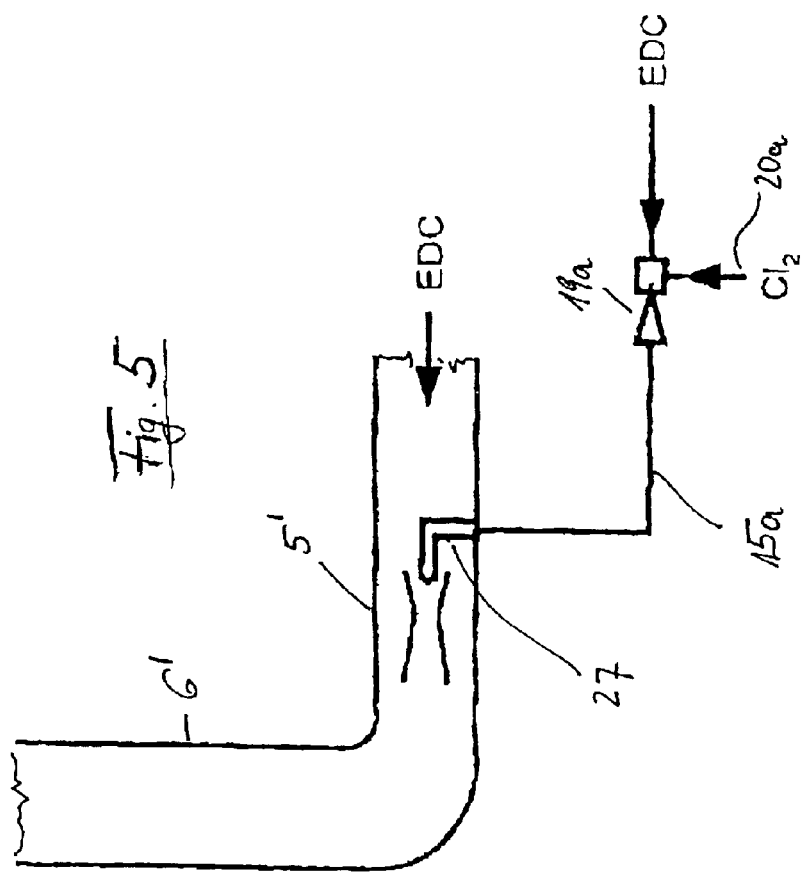

METHOD OF PRODUCING ETHYLENE (DI) CHLORIDE (EDC)

CROSS REFERENCE TO RELATED APPLICATIONS

Applicant claims priority under 35 U.S.C. §119 of German Application No. 199 10 964.8 filed Mar. 12, 1999. Applicant also claims priority under 35 U.S.C. §120 of PCT/EP99/07649 filed Oct. 12, 1999. The international application under PCT article 21 (2) was not published in English.

The invention relates to a method for producing 1,2-dichloroethane or ethylene (di)chloride (EDC), using a circulating reaction medium and a catalyst, whereby ethylene and chlorine are supplied to the reaction medium.

The production of 1,2-dichloroethane on a large technical scale is carried out by introducing the gaseous reaction partners chlorine and ethylene into a circulating reaction medium (1,2-dichloroethane in most cases) that contains a suitable catalyst (e.g. iron(III)chloride) in the dissolved form. In designing the reaction systems employed for said purpose, a distinction is made between concepts in connection with which the reaction medium is circulated by pumping, and those in conjunction with which the reaction medium is circulated by both the mammoth pumping effect of the gaseous reaction partners that are metered in, and the natural circulation that is produced by the reaction heat.

A system of the first type is described, for example in DE 19 05 517, DE 25 40 257, and DE 40 39 960 A1. In the case of said system, the reaction medium is circulated by pumping via an external circulation and first aspirates the gaseous chlorine by means of a liquid-jet gas compressor. Gaseous ethylene is subsequently fed in via a perforated gas distributor. The mixed stream so produced then flows through a packing of fillers or a static mixer, where the relatively large ethylene bubbles produced by the gas distributor are dispersed, so that the ethylene dissolves at an adequate rate and reacts with the already dissolved chlorine.

The use of a static mixer is described in EP 0 471 987 B-1. Thus the packing of fillers or the static mixer represent the actual reaction line.

In addition to aspiration and fine distribution or dissolution of the reaction partners, the stream circulated by pumping performs a further function: dissipation of the reaction heat. The reaction heat amounts to about 2,200 kJ/kg EDC, i.e. the amount of heat collected in the production of 1 ton of EDC suffices for generating approximately 1 ton of steam. The circulated amount therefore has to be large enough to prevent boiling from occurring along the reaction line.

In the system described in the patent documents cited above, the reactor content does not boil, but the hot circulating stream is rather divided in two partial streams. The lager part stream serves for indirectly heating columns, whereas the smaller part stream is partially relieved. The gaseous stream produced by the relief evaporation corresponds with the quantity produced and can be directly fed into a column for a purification treatment.

A special drawback of the known procedure consists in the fact that the stream circulated by pumping is very large, so that large pumps with high capacities are required, which conditions high investment and operating costs.

In the other system operating with natural circulation, the required circulation of the liquid is produced by the mammoth pumping effect of the gaseous reaction partners or by natural convection due to the liberated reaction heat. The circulation of the liquid can take place in this connection via an external pipeline or also in the reactor vessel itself.

Said method is described, for example in DE-OS 24 27 045. In said process, the reaction medium circulates via an external pipeline and the reaction partners are admitted into the circulating stream via gas distributors. The reaction mixture subsequently flows through a packing that represents the reaction line. The circulating amount can be controlled by means of a fitting. With the present concept, the reactor content is boiling. It is therefore necessary to assure through an adequate geodetic level and corresponding positioning of the reaction line and also through adjustment of a sufficiently large circulating stream that no boiling will occur along the reaction line. A drawback of said system is that the chlorine is not aspirated and compressed by a liquid-jet gas compressor, but has to be already available at a certain minimum pressure, which is often not the case, so that pre-compression of the chlorine may be required.

Both systems have in common that a local excess of chlorine may be present at the start of the reaction line, which favors the formation of higher-chlorinated by-products. This has its cause in the fact that chlorine is by multiple times more soluble in 1,2-dichloroethane than ethylene. This has the following consequences in both of the systems described above:

With the first system (forced circulation with pumps), the chlorine is immediately very finely distributed by the high shearing forces acting in the liquid-jet gas compressor, and is received already highly dissolved at the point where the ethylene is added. This means that an excess of chlorine is already on hand when the ethylene starts to dissolve.

With the second system (natural circulation), the added chlorine dissolves along the reaction line at a higher rate than the ethylene. An excess amount of chlorine is present at least at the start of the reaction line in that case as well.

The problem of the present invention is to provide a solution by which the catalytic chlorination of ethylene is made possible in a manner that is particularly gentle for the product, whereby the reaction heat generated in the course of the reaction is employed in a useful manner and the undesirable formation of highly chlorinated products such as tri-, tetra- and pentachloroethane in the reactor is largely avoided. Said benefits are combined with a plant concept that permits a modular type of expansion of the system at favorable cost.

In a process of the type specified above, said problem is solved according to the invention in that the ethylene or the chlorine gas is introduced into the reaction medium by means of microporous gas diffuser elements employed for producing gas bubbles having a diameter of from 0.3 to 3 mm.

Said special manner of introducing the gases into the reaction medium achieves an adequately fine distribution and thus an optimal production result. Introducing said gas bubbles with the size as defined by the invention is possible in a comparatively simple manner. Special devices for admitting the gas bubbles are specified farther below.

A contribution to the solution of the problem that is based on the same starting point consists in that the chlorine is dissolved in a cooled part stream of the reaction medium and then supplied to the main stream of the reaction medium. The problem as defined by the invention can be solved by said measure as well-, notably the catalytic chlorination of ethylene in a manner that is especially gentle for the product.

Finally, the invention makes provision that viewed in the direction of circulation of the reaction medium, ethylene is introduced into the circulating medium at a point upstream, and, after passing through a mixing and dissolving zone, chlorine is supplied to the reaction medium at a point farther downstream, whereby the ethylene (di)chloride that is liberated in the reaction of the chlorine and ethylene and evaporated by the reaction heat, is discharged from the reaction vessel in the gaseous state, whereas the residual amount remaining in the evaporation vessel is recycled into the reaction zone.

The method as defined by the invention permits achieving optimal results because the partners participating in the process each have adequate time to react. For example, the ethylene can pass through the free dissolution line located between the ethylene distributor, on the one hand, and the start of the chlorine distributor on the other, and is capable of dissolving completely owing to the small starting size of the bubbles produced by the microporous gas diffuser elements, so that the subsequent reaction takes place in solution.

Apart from providing for only one point at which the ethylene is added, it is, of course, possible also to make provision for several of such points of addition. In any case, the formed EDC first remains in the liquid phase and evaporates only within the zone of the surface of the evaporator vessel, whereby the evaporation cold is compensated by the reaction heat.

The reaction partners ethylene and chlorine may be diluted with inert gases.

The use of iron(III)-chloride as the catalyst, for example, can be recommended. For avoiding the formation of by-products, it is possible also to use, for example oxygen as an inhibitor.

Further developments of the procedure as defined by the invention are specified in the dependent claims, whereby it is useful to employ as the reaction medium, for example a medium predominantly containing 1,2-dichloroethane. As process parameters, it is recommended to adjust a temperature of about 75° to 200° C. and a pressure of about 1 to 15 bar in the mixing and reaction zone, and to control the rate of flow-through in such a way that the dwelling time of the reaction mixture in the mixing and reaction zone amounts to from −1 to 30 seconds.

Finally, provision is made, furthermore, that the chlorine is added to the main stream of the reaction medium at the end of the mixing and reaction zone, said chlorine having first been dissolved in an undercooled part stream of the reaction medium. Dissolving the chlorine in an undercooled part stream offers the advantage that a particularly large amount of chlorine is dissolved in that case, and is possible to make do with a comparatively small amount of liquid or with smaller pumps. The fact that the solubility of the chlorine is rising as the temperature is dropping is advantageously exploited in this manner.

Alternatively, it is possible also to make provision that the chlorine is dissolved in a separate liquid circulation, for example in 1,2-dichloroethane, and then added to the reaction medium.

Furthermore, for solving the problem, the invention make provision for a device for carrying out the method as defined by the invention. Said device is characterized by an evaporator vessel, a down pipe and a rising pipe, whereby provision is made in the riser in the direction of flow first for an ethylene feed, subsequently for a dissolving zone, and following the latter for distributor tubes for admitting chlorine into the main stream of the reaction medium, such chlorine having first been dissolved in a bypass stream of the reaction medium.

Further developments of the invention are specified in the dependent claims relating to the device as defined by the invention. For example, provision can be made in the flow path of the reaction medium for a circulation device for producing a forced circulation, and for controlling purposes for a throttling valve or the like. It has to be noted at this point that the natural circulation is a joint object of the present invention, whereby provision can be made for similar control elements in the flow path of such natural circulation.

As a further development of the invention, provision can be made for a bypass line for the reaction medium, such bypass comprising a pump, a heat exchanger for cooling said bypass part stream, a liquid-jet compressor downstream for aspirating and introducing gaseous or liquid chlorine into the bypass stream, and/or for a static mixer, as well as for a feed leading into a ring conduit with distributor tubes for feeding the bypass stream into the main stream.

So that the flow-through can be controlled in a very precise manner, the invention, furthermore, provides for a further development in that provision is made for an ultrasound measuring device for measuring the flow-through in the main stream, as well as for a control means for actuating a flow-through control valve or the like.

At least two risers comprising the installations as defined by the invention may be associated with one down pipe. Furthermore, a multitude of evaporator vessels comprising one or more down pipes and risers can be arranged according to the invention in a suitable manner, whereby one or more reaction zones are arranged in such a system in the one or more circulation pipelines.

Said further developments of the invention make it possible to design the device as a type of modular construction. It is advantageous for said purpose if each unit comprising an evaporator vessel, a down pipe and a riser with installations is designed in the form of a module with devices for coupling it with at least one adjacent module or a number of such modules. Another preferred embodiment is the one that comprises an evaporator vessel with a plurality of risers and down pipes, or with a central down pipe and a plurality of risers starting from said down pipe.

Other embodiments of the invention consist in that provision is made in the bypass for a mixer with a heat exchanger as one unit in terms of device, and/or that microporous gas diffuser elements are provided in the main stream for finely distributing the ethylene to be introduced, and/or that elements such as baffle plates, throttling valves or the like are installed in the reaction zone for rectifying the flow.

A further advantageous embodiment of elements of the device as defined by the invention consists in that upstream of the gassing elements, a device for rectifying the flow is arranged in the main stream for producing a uniform velocity profile, as well as for suppressing radial velocity components.

Further features, details and advantages of the invention issue from the following description as well as from the drawing, in which:

FIG. 2 is a partly enlarged cutout from the riser of the device as defined by the invention, comprising symbolically indicated installations.

FIGS. 3 and 4 are simplified sectional drawings according to lines III—III and, respectively, IV—IV in FIG. 2.

FIG. 5 shows a partial view of a pipe area with a driving jet nozzle, and

FIG. 6 shows a cutout of a part tube with a nitrogen feed nozzle.

Figure 1:
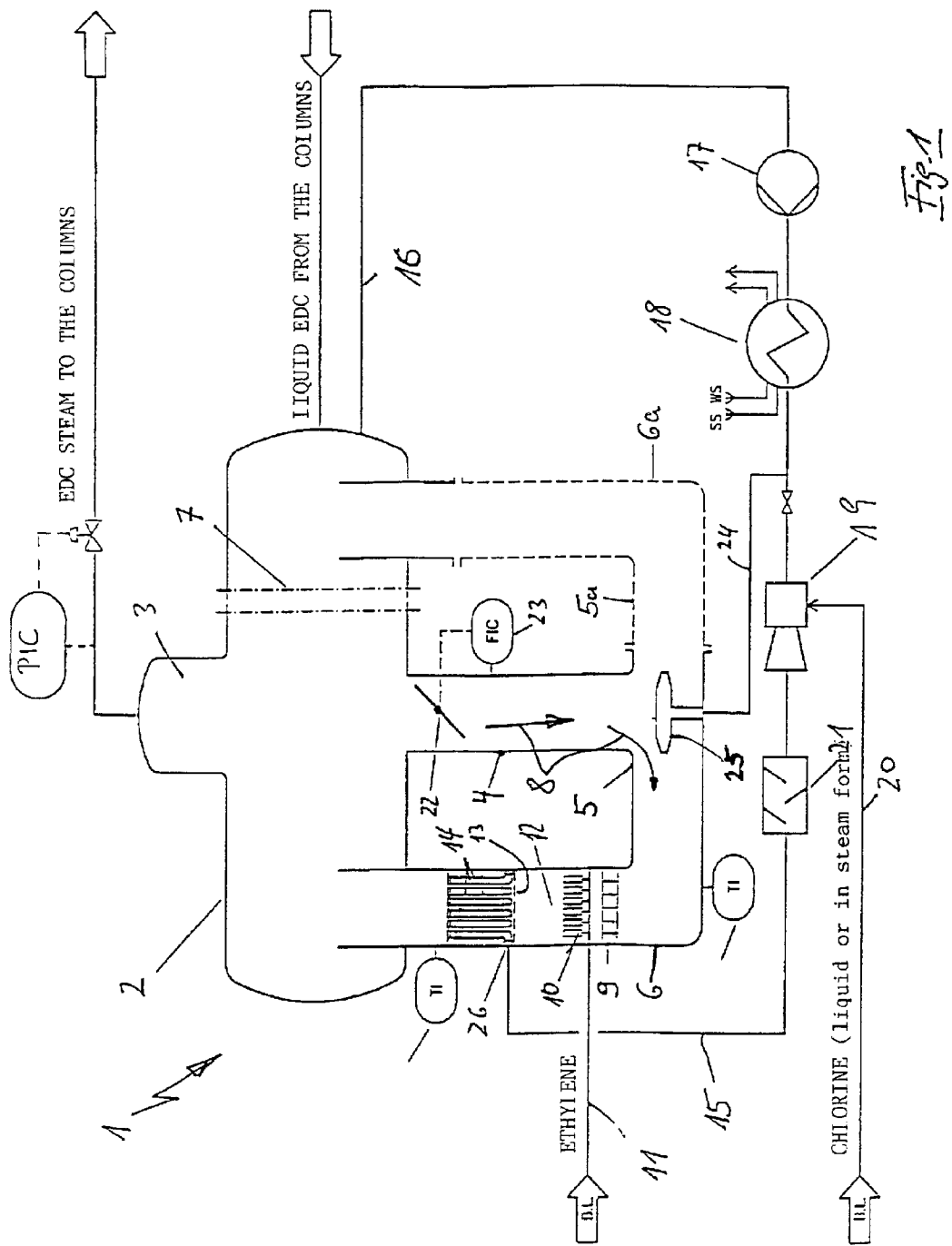
FIG. 1 is a simplified flow diagram of the device as defined by the invention.

The device for carrying out the method for producing EDC with the use of a circulating reaction medium is generally denoted in FIG. 1 by reference numeral 1 and substantially shown only symbolically and highly simplified.

FIG. 1 shows an evaporator vessel 2 with an indicated stream dome 3 and a down pipe 4 that merges via a transition line 5 into a rising pipe generally denoted by 6, said riser in turn feeding into the evaporator vessel 2. Following the down pipe to the right, FIG. 1 shows by a dash-dotted line that a transition line 5a and a rising pipe 6a are associated with said down pipe, whereby the evaporator vessel 2 is divided via the dash-dotted lines 7, which indicate that the device can be realized in the form of a modular construction, i.e. provision can be made for a plurality of risers on an evaporator vessel 2 that has been extended in a modular manner. Said evaporator also may comprise more than one down pipe-, if necessary, which, however, in not important in this connection.

FIG. 1 shows that the flow follows a defined direction either by natural or forced circulation, said direction being indicated in FIG. 1 by the arrows 6. After passing through the transition line 5, provision is made in the riser 6 in the direction of flow first for a flow rectifying device 9 in order to produce a uniform axial velocity profile and to suppress radial velocity components. Said flow-rectifying device 9 is followed by a series of the microporous gas diffuser elements 10, by way of which pearls of ethylene can be introduced into the circulating reaction medium via the line 11.

Thereafter, provision is made in the riser for a dissolution zone denoted by 12, which in turn is followed downstream by an installation 13 for producing a uniform flow, and for a feeding element 14 for feeding in chlorine dissolved in the reaction medium. The feed line for said reaction medium/chlorine mixture is denoted by 15.

Via a line 16, a part stream is tapped from the reaction medium as the bypass stream 16 and then supplied to a cooler 18 by a pump 17, whereby the chlorine supplied via the line 20 is admixed to said bypass stream via a liquid-jet compressor 19, whereby provision can be made in the flow path for a static mixer 21 as well.

For regulating the circulation, provision is made in the down pipe 4 for a symbolically indicated throttling valve 22. The position of said throttling valve is controlled, for example by means of an ultrasound measuring method for measuring the flow-through, said control being generally denoted by 23.

For the start-up operation, a part stream of the bypass stream 16 can be supplied via a line 24 to a distributor nozzle 25 which, in the transition zone 5 from the down pipe 4 to the riser 6, provides for the required flow, whereby the heat exchanger 18 can then be employed as a heater as well.

The arrangement and positioning of the gas diffuser element 10 as well as of the feed elements 14 for feeding the ethylene, on the one hand, and the reaction medium/chlorine mixture on the other, are shown in FIGS. 2 to 4 in slightly greater detail, with only examples being shown in said figures.

FIG. 2 in association with FIG. 4 shows that the microporous gas diffuser elements 10 are arranged in the form of a star in the interior of the riser 6 and acted upon by the line 11, whereby such an arrangement is not mandatory. The feed elements 14, on the other hand, are mounted on a ring channel 26, which is only indicated in FIG. 2 in association with FIG. 3 as well.

FIG. 5 shows the possibility for providing a nozzle 27 in the transition line, which in denoted here by 5'. The part EDC stream 15', into which the chlorine 20' was previously introduced, for example via a liquid-jet compressor 19', is introduced via said nozzle. Said part stream can be employed as a driving jet in order to support the flow in the loop reactor FIG. 6 shows the possibility for making provision for supplying small amounts of preheated nitrogen via a ring line 28, for example on the riser 6b, in order to prevent retardation of ebullition (flow surges), whereby the ring line 28 is provided with the candles 29 made of a rough porous material, as this is indicated in FIG. 6.

The described exemplified embodiment of the invention can, of course, still be modified in many different ways without vacating the basic idea of the invention. For example, the invention is in particular not limited to the special arrangement and embodiment of the gas diffusion elements 10 shown in the present case on the one hand, and the feeding elements 14 on the other, and is also not limited to a certain type of control system, although the control selected in the present case in particularly useful. The gas diffuser elements can be provided also in the down pipe because the dissolution of the ethylene may take place also in the down pipe, whereby the gas bubbles produced are transported downwards by the liquid stream (the velocity of the flow of the liquid produced by the circulation is greater than the velocity at which the gas bubbles rise.

What is claimed is:

1. A method of producing 1, 2-dichloroethane or ethylene (di)chloride (EDC) using a circulating reaction medium and a catalyst, whereby ethylene and chlorine are supplied to the reaction medium, comprising the steps of
   (a) introducing ethylene into the circulating reaction medium at a point upstream viewed in the direction of circulation of the reaction medium and, after passing the ethylene through a mixing and dissolving zone, completely dissolving the ethylene in the reaction medium stream; and
   (b) dissolving the chlorine in a cooled part stream of the reaction medium and subsequently supplying the chlorine to the main stream of the reaction medium further downstream;
   whereby the ethylene (di)chlorine liberated with the help of the reaction of chlorine and ethylene and evaporated by the reaction heat is discharged from the reactor vessel in the gaseous state, whereas the residual amount remaining in the evaporator vessel is recycled into the reaction zone.

2. The method according to claim 1 wherein the ethylene or chlorine gas is introduced into the reaction medium by means of microporous gas diffuser elements in order to produce gas bubbles with a diameter of 0.3 to 3 mm.

3. The method according to claim 1, wherein a medium predominantly containing 1,2-dichloroethane is used as time reaction medium.

4. The method according to claim 1, wherein a temperature of about 75° C. to 200° C. and a pressure of about 1 to 15 bar are adjusted in the mixing and reaction zone, and the flow-through velocity is controlled so that the dwelling time of the reaction mixture in the mixing and reaction zone amounts to about 1 to 30 seconds.

5. The method according to claim 1, wherein the EDC formed first remains in the liquid phase or evaporates within the zone of the surface of the evaporator vessel; whereby the evaporation cold is compensated by the reaction heat.

6. The method according to claim 1, wherein the chlorine is a parately dissolved in the liquid and supplied to the reaction medium.

* * * * *

UNITED STATES PATENT AND TRADEMARK OFFICE
CERTIFICATE OF CORRECTION

PATENT NO. : 6,841,708 B1
DATED : January 11, 2005
INVENTOR(S) : Benje

It is certified that error appears in the above-identified patent and that said Letters Patent is hereby corrected as shown below:

<u>Column 8,</u>
Line 17, after the word "is", please change "a parately" to read -- separately --.

Signed and Sealed this

Fifth Day of April, 2005

JON W. DUDAS
*Director of the United States Patent and Trademark Office*

UNITED STATES PATENT AND TRADEMARK OFFICE
CERTIFICATE OF CORRECTION

PATENT NO.     : 6,841,708 B1
DATED          : January 11, 2005
INVENTOR(S)    : Benje It is certified that error appears in the above-identified patent and that said Letters Patent is hereby corrected as shown below:

Title page,
Item [73], Assignee, should read:
-- Vinnolit Technologie GmbH & Co. KG --.

Signed and Sealed this

Seventh Day of February, 2006

JON W. DUDAS
*Director of the United States Patent and Trademark Office*